(12) United States Patent
Studer et al.

(10) Patent No.: US 6,193,756 B1
(45) Date of Patent: Feb. 27, 2001

(54) TUBULAR SUPPORT BODY FOR BRIDGING TWO VERTEBRAE

(75) Inventors: Armin Studer; Cosimo Donno, both of Winterthur (CH)

(73) Assignee: Sulzer Orthopaedie AG, Baar (CH)

( * ) Notice: Subject to any disclaimer, the term of this patent is extended or adjusted under 35 U.S.C. 154(b) by 0 days.

(21) Appl. No.: 09/140,577

(22) Filed: Aug. 26, 1998

(30) Foreign Application Priority Data

Sep. 30, 1997 (EP) .................................................. 97810721

(51) Int. Cl.$^7$ ........................................................ A61F 2/44
(52) U.S. Cl. ......................................................... 623/17.15
(58) Field of Search ............................ 623/17, 16, 17.15, 623/17.16; 606/61, 68; 403/61, 109

(56) References Cited

U.S. PATENT DOCUMENTS

| | | |
|---|---|---|
| 3,102,536 | 9/1963 | Rose . |
| 5,290,312 | 3/1994 | Kojimoto . |
| 5,531,792 * | 7/1996 | Huene ...................................... 623/16 |
| 5,571,192 * | 11/1996 | Schonhoffer ............................ 623/17 |
| 5,702,455 * | 12/1997 | Saggar .................................... 623/17 |
| 5,776,197 * | 7/1998 | Rabbe et al. ............................ 623/17 |

FOREIGN PATENT DOCUMENTS

| | | |
|---|---|---|
| 36 05 630 A1 | 9/1987 | (DE) . |
| 44 09 392 A1 | 9/1995 | (DE) . |
| 195 04 867 C1 | 2/1996 | (DE) . |
| 2 730 158 | 8/1996 | (FR) . |
| WO 94/18913 | 9/1994 | (WO) . |

* cited by examiner

*Primary Examiner*—Bruce Snow
(74) *Attorney, Agent, or Firm*—Townsend and Townsend and Crew LLP

(57) ABSTRACT

With the invention, tubular support bodies for bridging two adjacent vertebrae are shown. Two cages (1, 2) which are placed one within the other are provided with cut-outs, and each of them has a support flange (5) at the outer end face (6). A first cage (1) has at least three radially projecting protrusions (7) at its jacket (9*a*) which can be introduced into three axially extending lead-in channels (8) or a multiple thereof in the jacket (9*b*) of the other cage (2) in order to be able to reach latch-in positions (10, 11, 12) of different depths.

11 Claims, 3 Drawing Sheets

$0.01 < D - d < 0.2$ mm

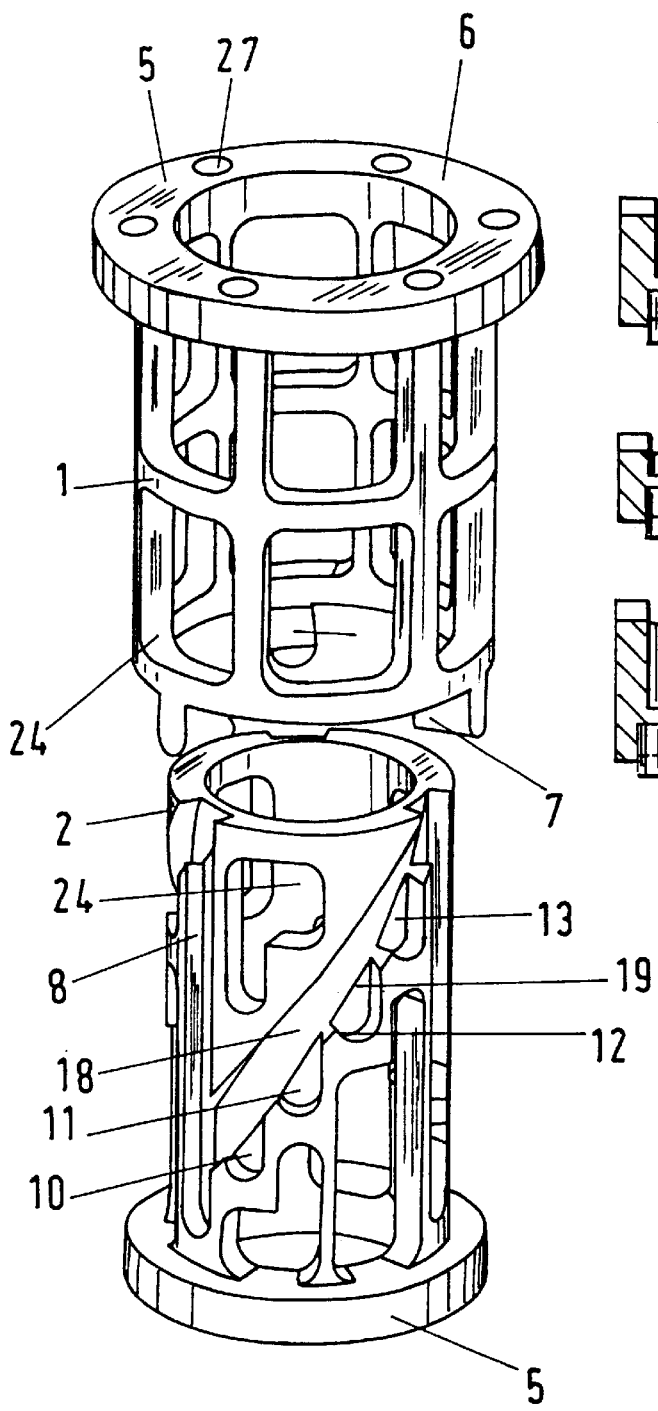
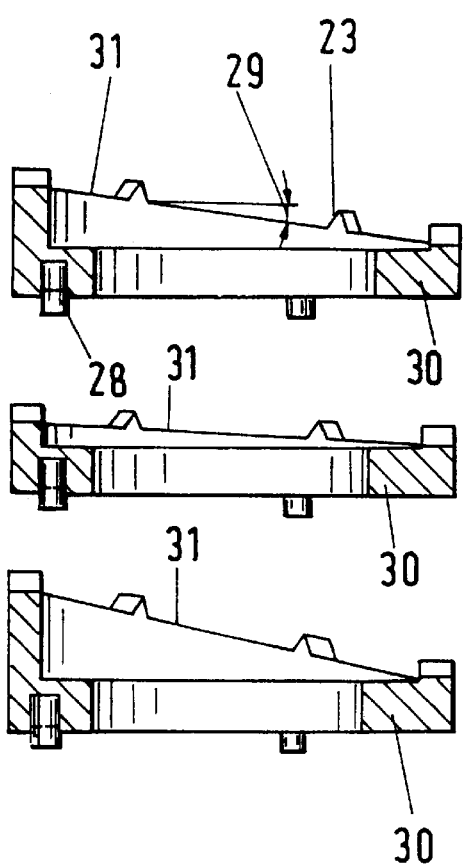

TUBULAR SUPPORT BODY FOR BRIDGING TWO VERTEBRAE

BACKGROUND OF THE INVENTION

The invention relates to a tubular support body for bridging two vertebrae having two cages which are placed one within the other and are provided with cut-outs and which each has a support flange at the outer front surface.

Support bodies of this kind are implanted in the region of the intervertebral discs when the intervertebral discs themselves no longer withstand the stresses which the adjacent intervertebral discs exert on them and a support body is required as a fill-in.

Support bodies of this kind are often designed as cages which are filled with autologous bone chips prior to the implantation. The cut-outs in the cages are herein chosen in such a manner that the bone tissue is captive, but that a supply of the bone tissue takes place through the cutouts after the implantation at the same time.

The patent specification DE 195 04 867 shows support bodies which can be pushed together to their insertion length prior to implantation. This has the disadvantage that the required construction length must be very precisely determined in advance. The orthopaedist must therefore have an entire arsenal of components in the operating room in order to assemble one of a suitable size.

A different design is shown in EP-A-0 693 274 with adjustable threads which determine the length of a support body at a suitable height and are subsequently secured by screws which penetrate radially into the thread. An embodiment of this kind has the disadvantage that it can actually be fixed only once due to the damage which arises at the thread. Achieving a certain bias force on the securing screws is possible only via a plastic deformation of the threaded passages at the support body.

SUMMARY OF THE INVENTION

It is an object of the present invention is to provide a multiply adjustable support body with few parts. This object is satisfied in that a first cage has at least three radially projecting lugs or protrusions at its jacket which can be introduced into three axially extending lead-in channels or a multiple thereof in the jacket of the other cage in order to be able to reach latch-in positions at different depths.

An advantage of the invention consists in that support bodies of different lengths can already be manufactured with two parts simply by pushing together and in that there is no danger that the push connection is released as long as a pressing force is present in the main load direction through the ligamenture or the weight. A further advantage consists in that the cut-outs at both cages can be matched to one another through definite latch-in positions in such a manner that the cut-outs align with one another in the region of covering and thus a supply of the bone chips lying within the cage and a growing-in can take place independently of the latch-in position. A further advantage consists in that no loose small parts such as securing screws or fastening screws are present in the field of operation.

Thus it is advantageous to provide the latch-in positions at the end of the respective lead-in channel with a clamping for the protrusions. This clamping can be done in the radial direction onto the protrusions, with the two cages being under a bias force with respect to one another in the radial direction and the spring action of the cages in itself producing a bias force. It is however also possible to clamp the protrusions in the latch-in position at their periphery through a reduction in the width of the lead-in channels. An elastic clamping is achieved here in that the lead-in channels have only a small wall thickness in the peripheral direction in the latch-in region and border on cut-outs which permit an elastic back resilience of the wall in the clamping region. The tolerances for a protrusions diameter "D" and for the clamping diameter "d" of the lead-in channel should be chosen in such a manner that 0.01 mm < D – d < 0.2 mm is satisfied. The clamping has the advantage that, in a setting prior to the insertion of the implant, it can be handled as a single-piece body for the insertion.

The support bodies can be provided at their outer ends with connection pieces which have an outer securing plane disposed at an inclination and which can be latched into the support body at different angles of rotation to compensate for deviations from parallelism between two adjacent vertebrae.

BRIEF DESCRIPTION OF THE DRAWINGS

FIG. 3 is, an exploded view of two cages, with the latch-in positions for a spigot being arranged on the lower side of a helical lead-in channel;

FIG. 8 shows, in a section, different adapter pieces for a cage in FIG. 3.

DESCRIPTION OF THE PREFERRED EMBODIMENT

Figure 1:
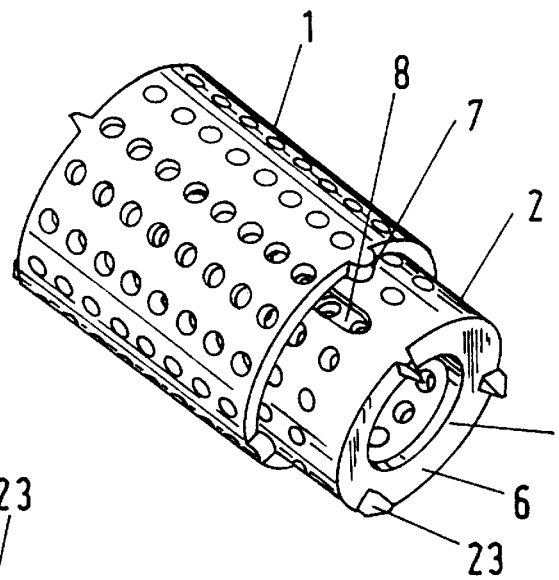
FIG. 1 is, a view of a tubular support body pushed together from two cages, with a separate lead-in channel being provided for each latchin position.

The figures show tubular support bodies for bridging two adjacent vertebrae. Two cages 1, 2 which are placed one within the other are provided with cut-outs and have a support flange 5 at the outer end surface 6. A first cage 1 has at its jacket 9a at least three radially projecting protrusions 7, which can be inserted into three axially extending lead-in channels 8 or a multiple thereof in the jacket 9b of the other cage 2 in order to be able to reach different latch-in positions 10, 11, 12.

Figure 5:
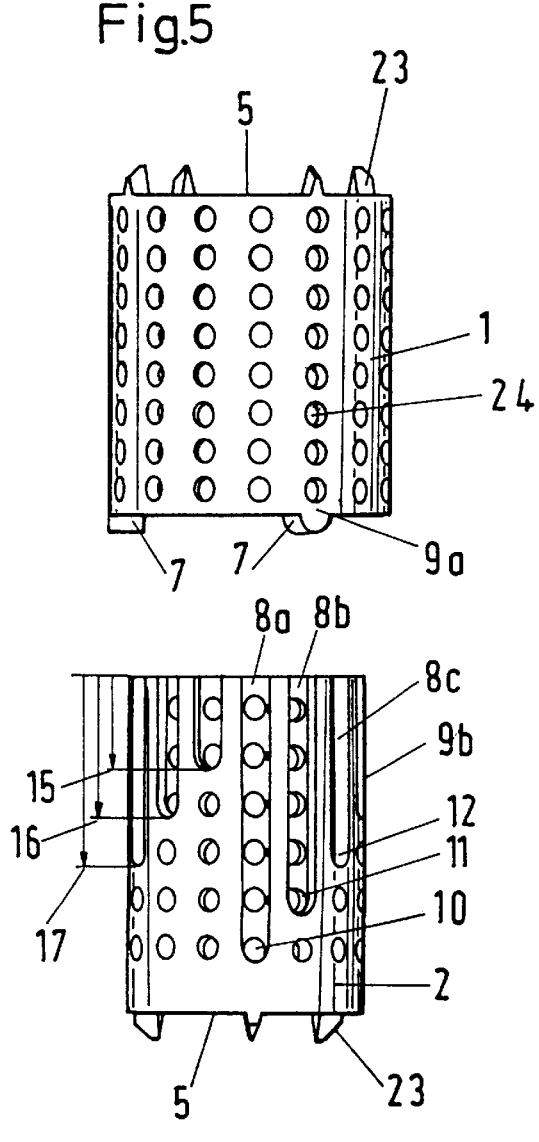
FIG. 5 is, a side view of the disassembled support body in FIG. 1.
Figure 4:
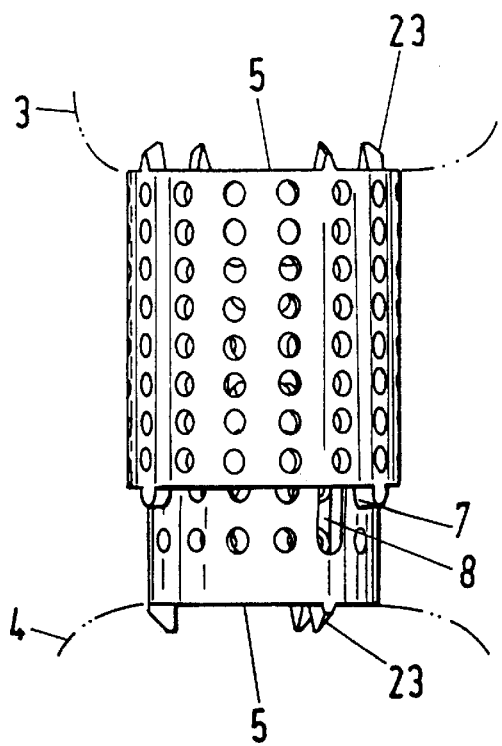
FIG. 4 is, a side view of the support body in FIG. 1 between two adjacent vertebrae.

In a first exemplary embodiment, FIG. 1, FIG. 4 and FIG. 5 show an outer and an inner cage 1, 2 of Titanium, which have a support flange 5 with projecting spikes 23 at their outer end surface 6. The inner cage 2 has lead-in channels 8, 8a, 8b, 8c at its outer jacket surface 9b which extend parallel to the axis of the tubular body and which have latch-in positions 10, 11, 12 at different depths 15, 16, 17 from the inner side. Both cages 1, 2 are provided with cut-outs 24 which align with one another in the different latch-in positions in order to obtain sufficiently large cut-outs for the supply of the enclosed bone chips. Three protrusions 7 which project radially inwardly and are displaced by 120° are provided at the outer cage 1 which are pushed in during assembly into lead-in channels 8a, 8b or 8c, which are likewise mutually displaced by 120° and have a suitable depth 15, 16, 17. When a latch-in position has been reached, the milled-in depth of the lead-in channels 8 decreases to such an extent that a radial clamping of the protrusions results. For the actual clamping, the elasticity of the cages 1, 2, which are radially deformed in opposite directions in the latch-in positions 15, 16, 17, is exploited. The clearance between the outer jacket surface 9b of the inner cage 2 and the inner jacket surface of the outer cage 1 is kept so large that the jacket surfaces do not touch one another in the plane of the three clamping points. The thus arising spring characteristic is shallower than during contact and places less stringent requirements on the dimensional tolerances in order to achieve a given clamping force. The clamping of the two cages can be released so that each of the possible depths 15, 16, 17 can be set in the operating room in order to subsequently stuff the support body with bone chips and to insert it between two vertebrae 3, 4 which have been wedged apart. If an intervertebral disc is still present between two vertebrae, it must have lateral cut-outs for the insertion of the, for example, pair-wise deployed support bodies.

Figure 2:
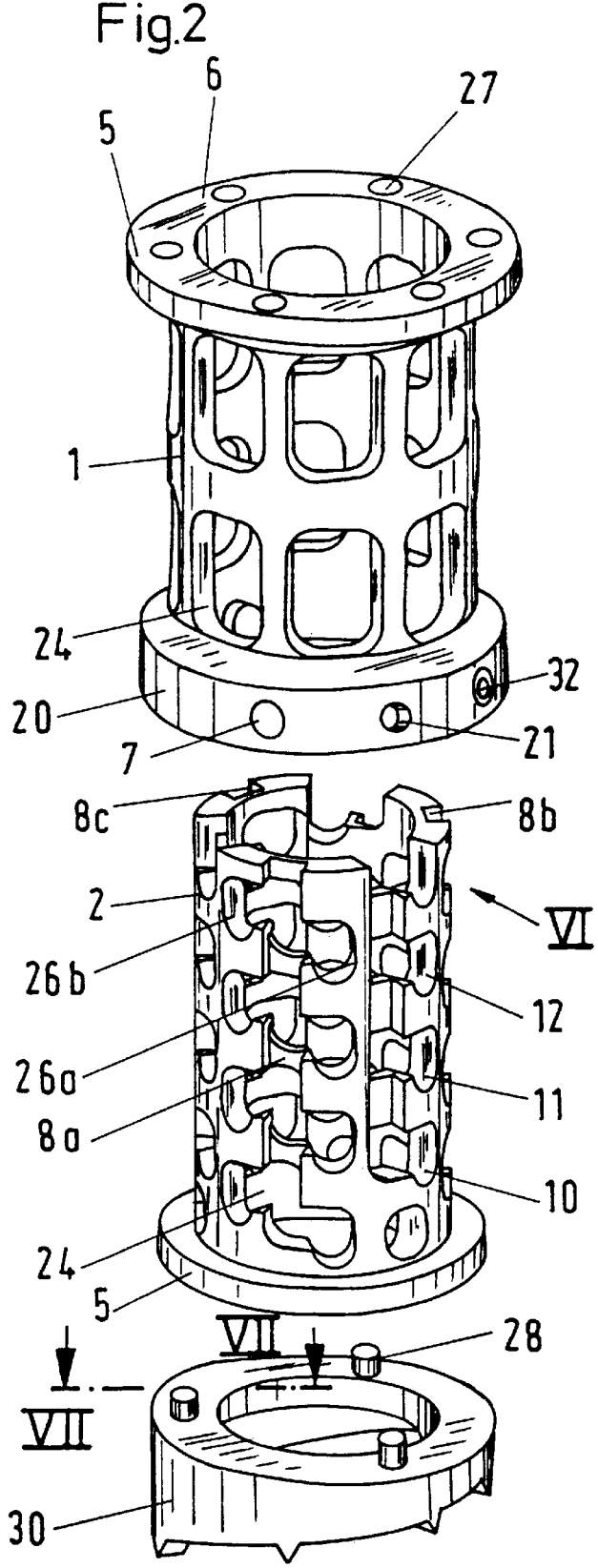
FIG. 2 is, an exploded view of two cages with an adapter piece, with the latch-in positions for a protrusion branching off to the left and to the right from a lead-in channel.
Figure 6:
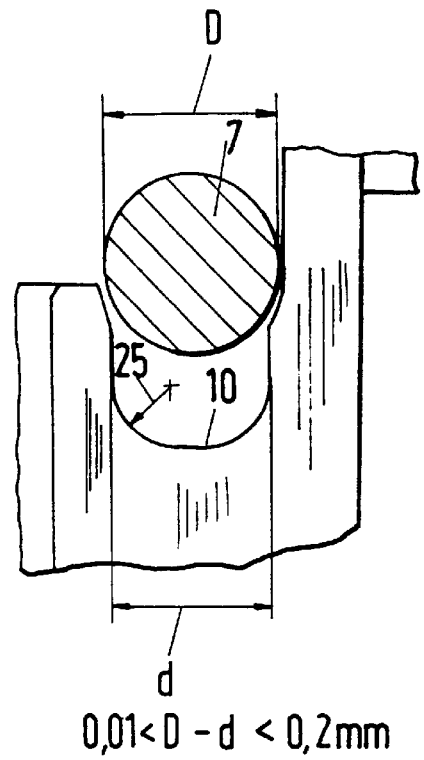
FIG. 6 is, an enlarged section from FIG. 2 which shows one of the clamping arrangements for a latch-in position.
Figure 7:
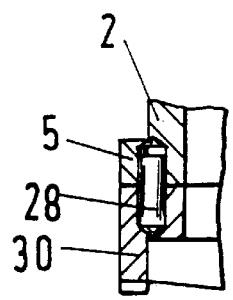
FIG. 7 is, a section through an adapter piece in FIG. 2 which shows the connection between the adapter and the cage.

A further exemplary embodiment in FIG. 2, FIG. 6 and FIG. 7 shows an outer cage 1 with a support flange 5 which has receiving bores 27 and is provided with a ring 20 in which three protrusions 7 are let in which are displaced by 120° and project radially inwardly. Radial bores 21 for adjusting tools are placed in the ring 20 and a countersunk securing screw 32 is optionally inserted. Cut-outs 24 in the outer cage 1 are chosen so large that the cut-outs 24 of the inner cage 2 are decisive for the smallest cross-section independently of the latch-in positions.

The inner cage 2 likewise has at its outer side a support flange 5 with receiving bores for possible adapter pieces 30. Three lead-in channels 8a, 8b, 8c are mutually displacedly arranged by 120°. Latch-in positions 26a, 26b to the left and to the right, which are described in more detail in FIG. 6, can be reached from each of these lead-in channels 8a, 8b, 8c. A protrusion 7 makes, from the lead-in channel 8a, 8b, 8c, first a rotational movement in the horizontal and is then lowered in a transition region into the actual latch-in position 10. In the lead-in channel and in the transition region the width of the channel is greater than the diameter D of the protrusion 7. only in the latch-in position is the channel width d smaller and satisfies the condition 0.01 mm < D − d < 0.2 mm. The precise amount D − d for the bias force in the latch-in position depends on the extent to which the channel walls can yield elastically. In the latch-in position 10 the protrusion 7 lies in contact at a lower point and at two lateral points. A conforming radius 25 between the horizontal and the vertical is less than the radius of the protrusion 7 in order that a clearance in the range of the conforming radius is present and definite points are thereby provided at which a force can act.

In FIG. 2 three further lead-in channels are provided at the inner cage 2, from which latch-in positions 10, 11, 12 branch off only to one side and themselves represent intermediate stages of the latch-in positions 26a, 26b branching off to both sides.

The bores 27 in the flanges 5 are displaced by 120°. Adapter pieces 30 suited to them are provided and can be anchored with pressed-in pins 28 in the flanges 5. A plurality of adapter pieces 30 are possible with different angles of inclination 29, as shown in FIG. 8.

FIG. 3 and FIG. 8 show a further system in which the inner cage 2 has three lead-in channels 8 displaced by 120° which are each connected to the adjacent lead-in channel by a further lead-in channel in the form of a helix. At the lower side 19 of these helical lead-in channels 18, latchin positions 10, 11, 12 in which the protrusions 7 are clamped in radially 13 or tangentially in accordance with a procedure described above necessarily branch off at different depths. If the filling of the cages with bone chips can be done in part after the insertion at the outer cage 1, this solution has the advantage that the cages 1, 2 can be pushed together in their lowest form via the lead-in channels 8 when being inserted and that a suitable latch-in position 10, 11, 12 can be reached after the introduction ween the two vertebrae by a rotation of the protrusion 7 along the helix 18. Together with different adapter pieces there is a good matching in the inclination 29 and in distance of the support surfaces 31 from the vertebrae. support surfaces 31 can be equipped with various spikes and recessions in order to effect an anchoring in the vertebra.

What is claimed is:

1. A tubular support body for bridging two adjacent vertebrae comprising first and second tubular cages placed one within the other and movable relative to each other, a first end of each cage extending beyond the other cage including a support flange and the cages including cut-outs for providing access into an interior of the cages, at least three protrusions on the first cage projecting radially toward the second cage, the second cage including at least two sets of at least three positioning surfaces each for engaging the protrusions on the first cage, the positioning surfaces of each set having like spacings from the first end of the second cage which differ from the spacing between the positioning surfaces of the other sets and the first end of the second cage, and at least three lead-in channels in the side of the second cage facing the first cage, extending in a generally axial direction from a second end of the second cage to the positioning surfaces and shaped to permit movement of the at least three protrusions into simultaneous engagement with the positioning surfaces of any one of the sets to thereby establish an axial spacing between the support flanges of the cages, whereby the axial spacing between the support flanges can be changed by engaging the protrusions with the positioning surfaces of a different set.

2. A tubular support according to claim 1 including a separate lead-in channel for each positioning surface.

3. A tubular support according to claim 1 including a plurality of positioning surfaces accessible from each lead-in channel, the plurality of positioning surfaces being associated with respective sets of positioning surfaces, and wherein the first and second cages are rotatable with respect to each other for engaging the at least three protrusions with the positioning surfaces of a selected one of the sets of positioning surfaces.

4. A tubular support according to claim 3 wherein the positioning surfaces associated with each lead-in channel are displaced from the lead-in channel in a circumferential direction of the cages.

5. A tubular support in accordance with claim 1 wherein each lead-in channel has the shape of a spiral extending about a portion of the side of the second stage facing the first stage, and wherein the positioning surfaces are disposed below a lower side of the spiral-shaped lead-in channel, and including a branch channel for each positioning surface permitting movement of the protrusions from the lead-in channel to the positioning surfaces of a selected set of positioning surfaces.

6. A tubular support according to claim 3 wherein the first cage includes radial bores for inserting an adjusting tool.

7. A tubular support according to claim 1 wherein the first cage includes a radially oriented threaded bore, and including a screw threaded into the bore for securing the cages to each other when the protrusions engage a set of positioning surfaces.

8. A tubular support according to claim 1 wherein the engaging surfaces are concave walls contiguous with spaced-apart side walls which define a channel in communication with the lead-in channel for movement of the protrusions from the lead-in channel into engagement with the positioning surfaces, and wherein a portion of the side walls contiguous with the positioning surfaces have a spacing which is between 0.01 to 0.2 mm smaller than a diameter of the protrusions.

9. A tubular support according to claim 1 including at least one adapter piece for connection to at least one support flange, wherein the at least one support flange has axially oriented bores, and wherein the at least one adapter piece has axially oriented pins for insertion into bores to permit connection of the at least one adapter piece to the at least one support flange at different angular positions.

10. A tubular support according to claim 9 wherein an end of the at least one adapter piece opposite the pins has an end surface which is angularly inclined relative to the at least one flange.

11. A tubular support according to claim 1 including a transition channel between each positioning surface and the associated lead-in channel for moving the pin between the lead-in channel and the positioning surface, the transition channel having a bottom surface and the protrusion having a radial length, the bottom surface of the transition channel being displaced in a radial direction towards the protrusion to effect a clamping of the protrusion by the bottom surface of the transition channel as the protrusion is moved into engagement with the positioning surface.

\* \* \* \* \*